US008848189B2

(12) United States Patent
Atkin et al.

(10) Patent No.: US 8,848,189 B2
(45) Date of Patent: Sep. 30, 2014

(54) METHOD AND DEVICE FOR EXPRESS ANALYSIS OF ACETONE TRACES IN GASES

(75) Inventors: Benjamin Atkin, North Miami Beach, FL (US); Vadim Goldshtein, Har Hevron (IL)

(73) Assignee: PositiveID Corporation, Delray Beach, FL (US)

( * ) Notice: Subject to any disclaimer, the term of this patent is extended or adjusted under 35 U.S.C. 154(b) by 1104 days.

(21) Appl. No.: 12/471,935

(22) Filed: May 26, 2009

(65) Prior Publication Data

US 2009/0290161 A1 Nov. 26, 2009

Related U.S. Application Data

(60) Provisional application No. 61/055,480, filed on May 23, 2008.

(51) Int. Cl.
*G01N 21/78* (2006.01)
*G01N 33/497* (2006.01)
*G01N 33/49* (2006.01)

(52) U.S. Cl.
CPC .......... *G01N 21/78* (2013.01); *G01N 2201/062* (2013.01); *G01N 2201/0221* (2013.01); *G01N 33/497* (2013.01); *G01N 33/49* (2013.01)

USPC .......................................... 356/433; 600/532

(58) Field of Classification Search
None
See application file for complete search history.

(56) References Cited

U.S. PATENT DOCUMENTS

| 4,931,404 | A  | * | 6/1990 | Kundu .......................... 436/128 |
| 5,055,270 | A  | * | 10/1991 | Consadori et al. .............. 422/98 |
| 2004/0236244 | A1 | * | 11/2004 | Allen et al. .................... 600/532 |
| 2005/0084921 | A1 | * | 4/2005 | Cranley et al. ................. 435/25 |

OTHER PUBLICATIONS

Galassetti et al. Breath Ethanol and Acetone as Indicators of Serum Glucose Levels. Diabetes Technology & Therapeutics 2005, vol. 7, No. 1, pp. 115-123.*
Wang et al. (Measurement Science and Technology, 2007, p. 2731-2741).*

* cited by examiner

*Primary Examiner* — Agnieszka Boesen
(74) *Attorney, Agent, or Firm* — Steven M. Greenberg, Esq.; Kara A. Brotman, Esq.; CRGO Law

(57) ABSTRACT

A device, system, and method for measuring acetone levels exhaled from a patient and correlating the measured level to a blood glucose concentration.

7 Claims, 11 Drawing Sheets

METHOD AND DEVICE FOR EXPRESS ANALYSIS OF ACETONE TRACES IN GASES

INDEX TO RELATED APPLICATIONS

This application claims benefit of U.S. Provisional Patent Application No. 61/055,480, filed May 23, 2008, the disclosure of which is incorporated herein by reference in its entirety.

BACKGROUND OF THE INVENTION

For many person, would need to measure and monitor blood glucose levels is very important. Conventionally, a sample of blood needs to be drawn and placed in a measuring device in order to accurately measure in vivo blood glucose concentrations.

There is a need to develop a non-invasive technique to accurately measure in vivo blood glucose concentrations.

The device and method of the present invention addresses this need.

BRIEF SUMMARY OF THE INVENTION

The invention relates to the development of technical means for chemical analysis of acetone in the air, namely portable devices for quantitative analysis micro amounts of acetone in exhaled air, primarily the indirect noninvasive blood glucose or insulin monitoring in human blood.

There are invasive devices for determining the content of glucose in the blood of diabetics, athletes, and pregnant women. These devices have substantial disadvantages, that limit their use. Primarily, these devices require damage to blood vessels, when drawing blood samples; moreover (except chromatographic analysis) they do not give necessary precision.

It is known that a larger quantity of acetone vapors contained in exhaled air of diabetics, pregnant women, people engaged in heavy physical labour, athletes at high physical loads.

It is also known that the concentration of acetone in exhaled air correlates with the content of glucose in the blood. In other words, the acetone is a reliable biological marker that allows control of glucose in the blood.

As established by biochemical studies, glucose in the blood is one of the main suppliers of energy to the body. If the blood has not enough insulin, which transports glucose molecules to the cells of the body (diabetes), or if glucose is expired (because high physical activity), the body begins the process of oxidation of fats. It fills a deficit of energy. But the oxidation of fats results in acetone as a by-product. This is the reason for increasing of the acetone content in the exhaled air.

Thus, the increasing of acetone in the exhaled air of diabetics shows a deficit of insulin in the blood. In the case of people engaged in heavy physical labor, acetone is demonstration of glucose deficit in the blood.

For people with diabetes, increasing of the acetone content in the exhaled air may be a signal for insulin injections. For people of heavy physical labor, increased acetone content in the exhaled air may be a signal to take additional products that contain sugar or glucose.

From numerous scientific publications it is well known that the concentration of acetone in exhaled air is correlated with the content of glucose in the blood. In other words, the acetone is a reliable biological marker for monitoring the content of glucose in the blood.

There are devices for noninvasive determining of the glucose content in the blood of people with diabetes. These devices also have disadvantages, which do not allow to use them widely. The main drawback of is the lack of precision and selectivity in relation to acetone.

The lack of precision—is the main drawback of the mentioned devices, as well as incorrect and inaccurate information about the content of glucose in the blood can lead to serious consequences for the patient.

For example, one known device is a method that uses cavity ring-town spectroscopy. Through a small camera, fitted with mirrors, air filled air with vapor of acetone, the beam of infrared laser is given. The beam is reflected by mirrors. This mirror method does not provide an opportunity to build a simple and reliable portable device.

A few noninvasive devices for determining glucose in the blood by determining the concentration of acetone in exhaled air are described in the literature. They are based on direct determining of acetone's concentration by optical methods. These devices are not optimal because they have low accuracy, are complicated, and cumbersome.

The present invention has created a handheld portable device, which will determine the concentration of acetone in exhaled air with a minimum content of acetone 3-5 mg/liter with an accuracy that will satisfy doctors and patients.

In one embodiment, the present invention is a device for measuring the concentration of acetone in exhaled air in order to determine the content of glucose in the blood, comprising:

(a) an inlet for expirated air;
(b) a dosator for receiving air from said inlet;
(c) an actuator for receiving air from said dosator with substantially the same volume for each measurement, said actuator interrupts air from said inlet when said dosator reaches a specified volume;
(d) a chemical cell containing a solution;
(e) a light emitter constructed and arranged for emitting light to pass through and spectrally analyze said solution;
(f) an optical sensor; and
(g) a microprocessor;
wherein said microprocessor produces an output correlating measurements of said optical sensor with blood glucose concentration.

The device has an actuator that controls a valve that fills said dosator with a predetermined volume of gas. The actuator controls a either or both of a valve that fills said dosator with a predetermined volume of gas and a valve that releases gas from a filled dosator into a chemical cell.

The device of claim 1 wherein said chemical cell contains a solution to selectively react with acetone from expired air. The solution contains a solute selected from Sodium Iodate, Sodium Nitroprusside, Metadiamine, Phenyl-hydrazone, Furfural, o-Nitrobenzaldehyde, or combinations thereof.

The device further comprises an output of a numerical value, wherein said numerical value is produced by said microprocessor and correlates the difference in optical absorbance of an unreacted chemical cell solution with a chemical cell solution reacted with acetone from exhaled air to produce an output congruous with blood glucose concentration. The output is displayed on a screen, transmitted wirelessly to a receiving device, or combinations thereof.

The present invention further includes a method for determining acetone concentration in exhaled air and correlating said acetone concentration with blood glucose levels, said method comprising:

(a) providing a device according to the invention;
(b) initiating a blank reading spectral of said chemical sensor solution;

(c) instructing a user to inhale and hold their breath for about 3-5 seconds;

(d) having said user exhale into an inlet of said device;

(e) taking a spectral reading of said chemical cell solution after reaction with acetone in expired air;

said device measures the change in absorbance from said blank reading with said spectral reading after reaction of said chemical cell solution with acetone from expired air and said device produces an output whereby said difference in absorbance is correlated with blood glucose concentration of said user.

DETAILED DESCRIPTION OF THE PREFERRED EMBODIMENTS

Figure 1:
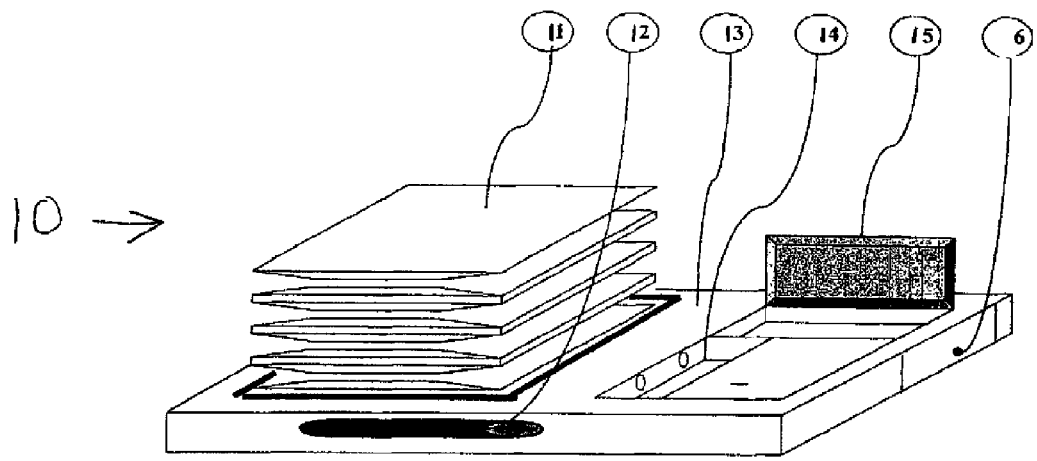
FIG. 1 is a top perspective view of the device.
Figure 2:
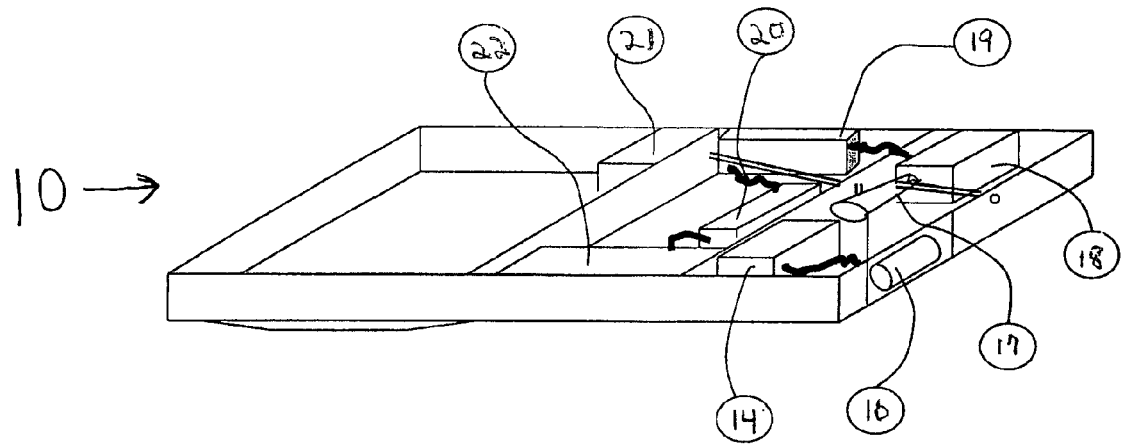
FIG. 2 is a bottom perspective view of the device.

Device 10 has an inlet 12 that directs exhaled air from a person into first tube 26 and ultimately into dosator 11. Dosator 11 holds exhaled air until dosator 11 if filled. An actuator 21 closes a valve when dosator 11 is filled such that the volume delivered to the measurement parts of the system is substantially constant. The actuator 21 is either mechanical or electrical and is calibrated to close a valve based on a predetermined volume of exhaled air in dosator 11. When dosator 11 is filled, and valve is closed, actuator 21 directs exhaled air from within dosator 11 through second air tube 27 and into chemical cell inlet 28. Chemical cell 23 is housed in cell cavity 14 formed in device housing 13. Chemical cell 23 has a sensor solution for selectively reacting with components of exhaled air. Chemical cell 23 is positioned such that it is between light emitter 25 and optical sensor 17. A beam of light 32 from light emitter 25 passes through chemical cell 23 and is detected by optical sensor 17. Optical sensor 17 is operatively connected with a microprocessor 22 and an electrical amplifier 20. Microprocessor 22 received light absorbance measurements from optical sensor 17 and using programmed correlation information, assigns a numerical value to acetone concentration. (A converter 19 converts the optical signal into an electrical signal.) The acetone concentration is processed using a mathematical algorithm to produce a correlation with conventional blood glucose concentration. Screen 15 displays a numerical value of blood glucose concentration based on the concentration of acetone in exhaled air.

Chemical cell 23 is a truncated cone and has solution 35 filled therein to level such that air is present above solution 35 in the interior of chemical cell 23.

Chemical cell 23 is a truncated cone. This configuration is advantageous as the shape reduces the scattering and focus beam of light from the light emitter 25. This reduction in scattering allows the maximum amount of light from the light emitter 25 to reach optical sensor 17. Other form shapes lacks this advantage.

Chemical cell outlet 30 has valve 31 that regulates the rate at which air exits chemical cell 23. Air that exits Chemical cell outlet 30 and valve 31 is vented to the atmosphere. In a preferred embodiment, device 10 has a second air tube 27 that is a capillary with a diameter of 30-50 microns. In solution 35, which is a water-alcohol solution of sodium-nitroprusside and sodium hydroxide, a foam is not formed, and air bubbles with diameter of 50-70 microns pass through the solution 35. The solution 35 itself remains in the chemical cell 23.

The device of the present invention is constructed and arranged to carry out an inventive method through a novel system.

The device, system, and method of the invention comprise:
Chemical cell 23 that can form a complex chemical compound with acetone (this compound is determined by a spectral method in the near UV spectral region),
Sampling exhaled air using a constant-volume container,
Receiving an analytical result, using a novel cell design.

Chemical cell 23 is a mini-cell, this is filled with solution 35 of an organic compound, easily quickly and selectively reacting with acetone. The product of interaction acetone with organic compounds is forming a color complex, defined by spectral method.

The analytical result is achieved by the registration of a molecular spectrum, followed by intensification of an electrical signal.

Figure 3:
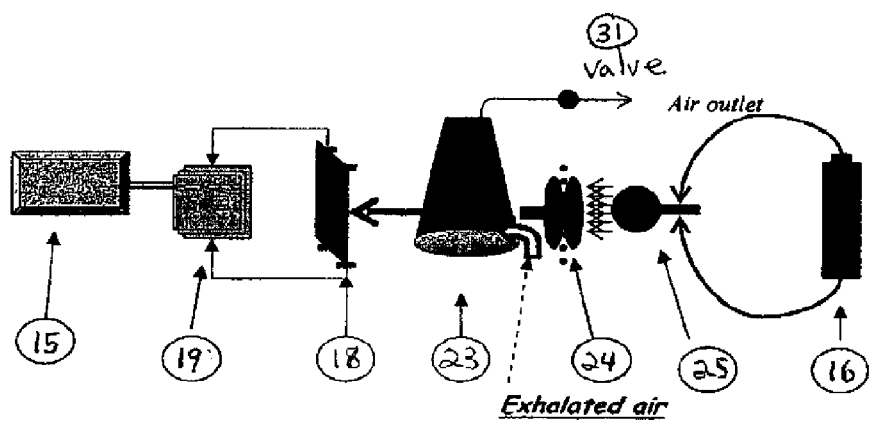
FIG. 3 is a block scheme of the measurement system.
Figure 4:
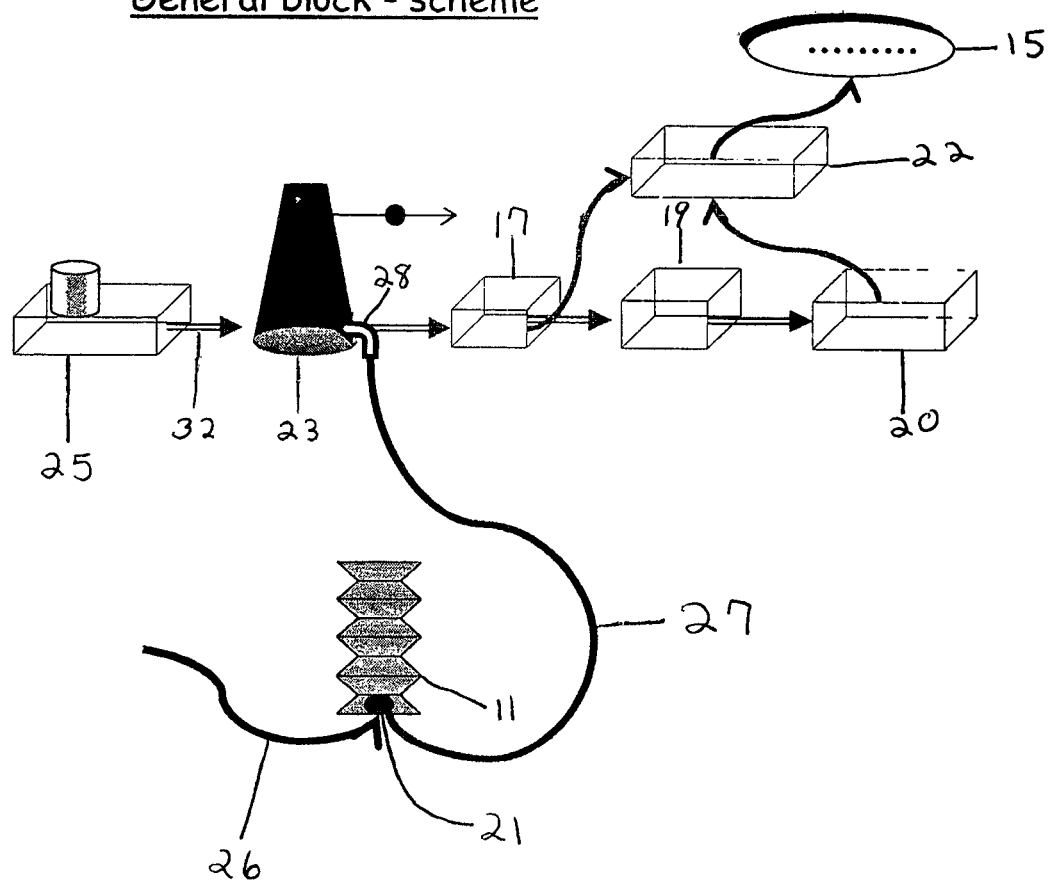
FIG. 4 is a block scheme of the measurement system.
Figure 5:
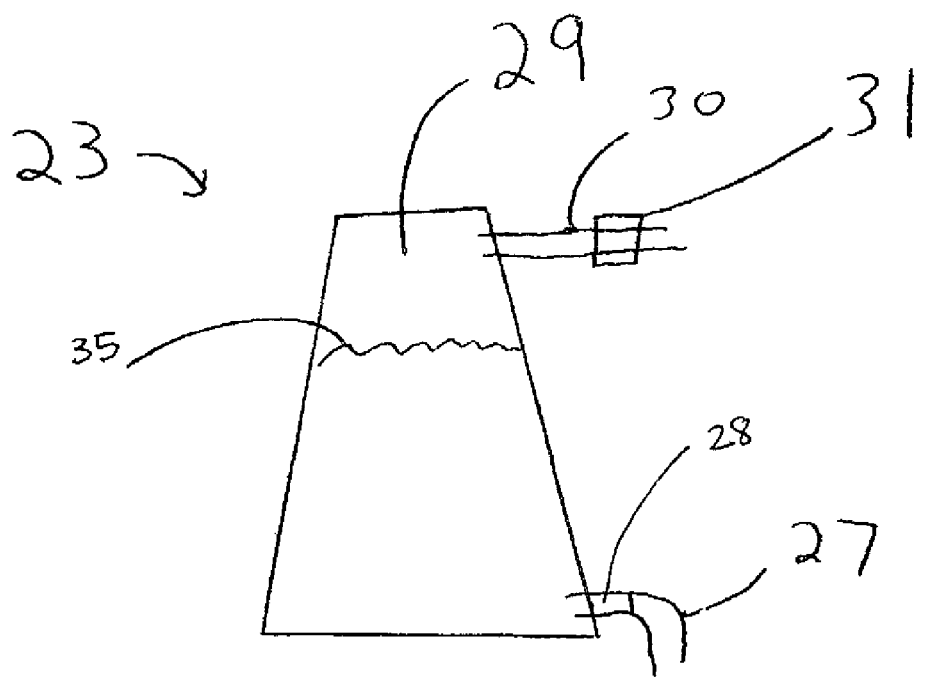
FIG. 5 is a cross section of the chemical cell.

The scheme of the device is represented in the FIGS. 3-5. The device works as follows.

Exhaled air enters into the inlet 12 of device 10. Dosator 11 is a bellow or balloon type structure that is filled to a fixed volume. Once dosator 11 is filled, an actuator 21 closes a valve to restrict any additional air from entering dosator 11 and a valve is opened by the system automatically sends air through second air tube 27 to interact with a solution 35 in chemical cell 23.

The solution 35 is a chemical solution of an organic compound, easily, quickly and selectively reacting with acetone. The solution 35 is placed in a chemical cell 23 that is preferably a mini-cell.

In chemical cell 23 a foam will not be formed. The air leaves the chemical cell 23 through cell outlet 30, not taking the chemical reagents from the solution 35 because of a very low surface tension of the solution 35. In addition, the design of the chemical cell 23 and the input and output air's system will protect against the loss of reagents from the chemical cell 23.

The system is constructed and arranged such that the presence of air entering chemical cell 23 through chemical cell inlet 28 activates the system. Once the air has passed through the solution 35 of the chemical cell 23, the measurement system turns on.

Acetone, which is one component of exhaled air, quickly and quantitatively reacts with the solution 35, resulting in a new chemical complex compound, suitable for the precise definition by spectral methods.

A beam of light 32 from light emitter 25 passes through a filter-monochromator 18 (i.e. a monochromatic screen), after that through the solution of the reacted solution 35, and said beam falls upon an optical sensor 17 that is a photometer photosensitive element. Optical sensor 17 produces an electric signal that is intensified in an electrical amplifier 20, and the signal is processed by microprocessor 22 to ultimately be displayed on screen 15. A battery 16, which can be covered by a housing cover 6, provides power.

The light emitter 25 is selected based on correlation with the maximum emission needed in the field. In the examples described herein, light emitter 25 is an LED-7 which has a maximum emission correlating with sodium nitroprusside absorbance. If other chemical sensors are used, other sources of emission are selected. Selection of a light emitter 25 is based on those light sources with a maximum emission that coincides or is close to the field of absorption of the particular chemical cell 23.

Figure 10:
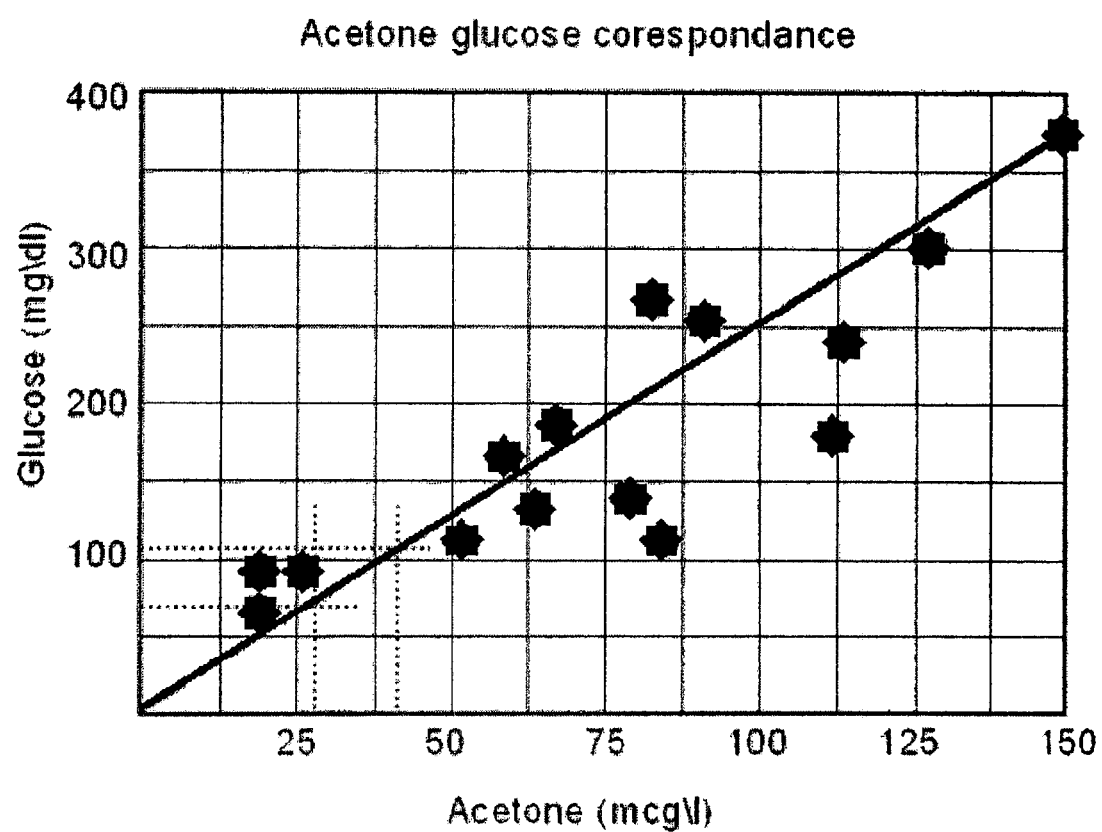
FIG. 10 is a scatterplot with linear representation of best fit line correlating blood glucose concentration with acetone concentration in exhaled air.

In the examples herein, the light source (LED-7) used as light emitter 25 in the present invention has a constant spectral characteristic as shown in FIG. 10. While passing the beam of light through the solution 35 of the chemical cell 23, the partial absorption of the emission occurs in the field of 380-420 nm. After the interaction of solution 35 with acetone, beam from the light emitter 25 passes again through the solution 35. As the acetone takes out the portion of the chemical cell 23 (proportional to the concentration of acetone) from this spectral region (380-420 nm), the second absorption in the 380-420 nm is lower than in the first case. The difference between the two absorptions gives the change in the concentration of chemical sensor and proportionally—the concentration of acetone in 1 liter of breath.

Monochromatic screen is an optical filter 24 that is a transparent color film, which transmits a narrow interval of optical emission within approximately 350-450 nm. A monochromatic screen (filter) will be used to remove unwanted optical "noise" and increase the sensitivity of the device.

In order to obtain reproducible results of air sampling, a patient needs to inhale air into the lungs, keep the air in the lungs for 3-5 seconds, and then exhale out the air into inlet 12 where expirated air enters device 10.

Device 10 measures the concentration of acetone in air introduced into the device in a range from about 3-5 mg/liter. The present invention has discovered the range of acetone concentration of about 3-5 mg/liter is sufficient for accurate correlation with glucose concentrations in the blood.

There are several organic compounds that will achieve the desired result. The present invention contemplates selection of at least one organic compound to carry out the objective of the present invention. The reaction product obtained from the interaction of acetone with at least one organic compound forms a color complex, defined by spectral method.

The device, system, and method of the present invention utilizes particular chemical reagents capable of rapid interaction with traces of acetone in exhaled air. The suitable reagents include, but are not limited to:
Sodium Iodate,
Sodium Nitroprusside,
Metadiamine,
Phenyl-hydrazone,
Furfural, and
o-Nitrobenzaldehyde.

The stoichiometric calculation of concentrations of sodium nitroprusside and sodium hydroxide was made. As a base, the actual concentrations of acetone (5 to 80 mcg/liter of breath) were used. The resulting concentrations of both reagents are necessary and sufficient to capture any amount of acetone in the specified limits.

For other chemical sensors similar stoichiometric calculations can be made.

In a preferred embodiment, the device, system, and method of the present invention utilizes the following reaction scheme:

REACTION SCHEME 1

Reaction with nitroprusside

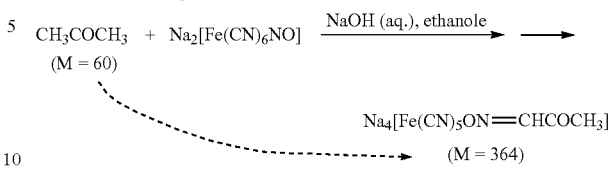

Reaction with furil aldehyde

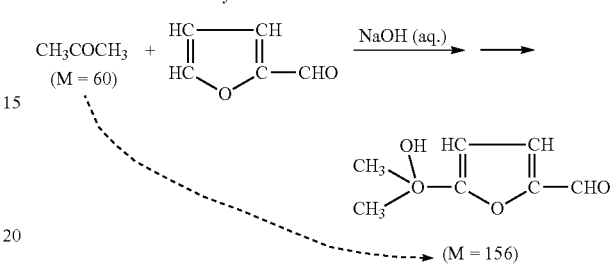

Reaction with iod

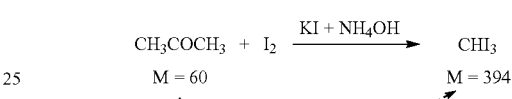

Reaction with salizylic aldehyde

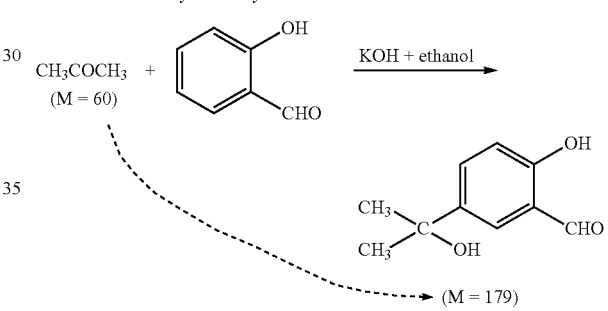

The device 10 has microprocessor 22 incorporated and operatively associated with all the components of device 10.

Microprocessor 22 provides the following functions and other functions as needed:
Pneumatic System Control
Fixing the amount of breath in dosator 11,
Change the actuator 21 for the air flow,
Control the speed of air passing through the solution 35 of the chemical cell 23.
Optical—Chemical System Control
Turning on a light emitter 25,
Recording of the optical sensor 17, such as, for instance, an optical diode.
Reform of Electrical Signal to Device Index
Recalculation and correlation of the electrical signal from an optical sensor 17 to the concentration of acetone,
Recalculation and correlation of the concentration of acetone detected to the concentration of glucose in blood.
Sending the result to the screen 15 of the device 10.
Sending results by e-mail.

The microprocessor is contemplated to have appropriate transmission mechanism to wirelessly transmit by email, text message or other wireless transmission, the results of a particular test to an email or server.

Control of Device Systems
Turning on the device,
Control sequencing of device work
Turning off the device.

Example 1

Sodium hydroxide and sodium nitroprusside are dissolved in a mixture of water and ethanol (a ratio of 50:50) to create a solution 35. The use of water-ethanol mixture as a solvent prevents a neutralization of sodium hydroxide by carbon dioxide (carbon dioxide is a part of the exalted air).

The solution 35 in the amount of 0.5 ml is poured into the chemical cell 23. The chemical cell 23 is a hollow truncated cone, made of transparent plastic. The entrance for the air, the chemical cell inlet 28, is in the wide part of the cone of chemical cell 23, and in the narrow part there is a chemical cell outlet 30 for air that is regulated by an valve 31 that ultimately vents air from the chemical cell 23 to the atmosphere. Chemical cell 23 is oriented vertically in the optical measurement system of device 10. The wide part of the chemical cell 23 is facing down, to the source of light, a light emitter 25. The narrow part of the chemical cell 23 is facing up—to an optical sensor 17.

Figure 11:
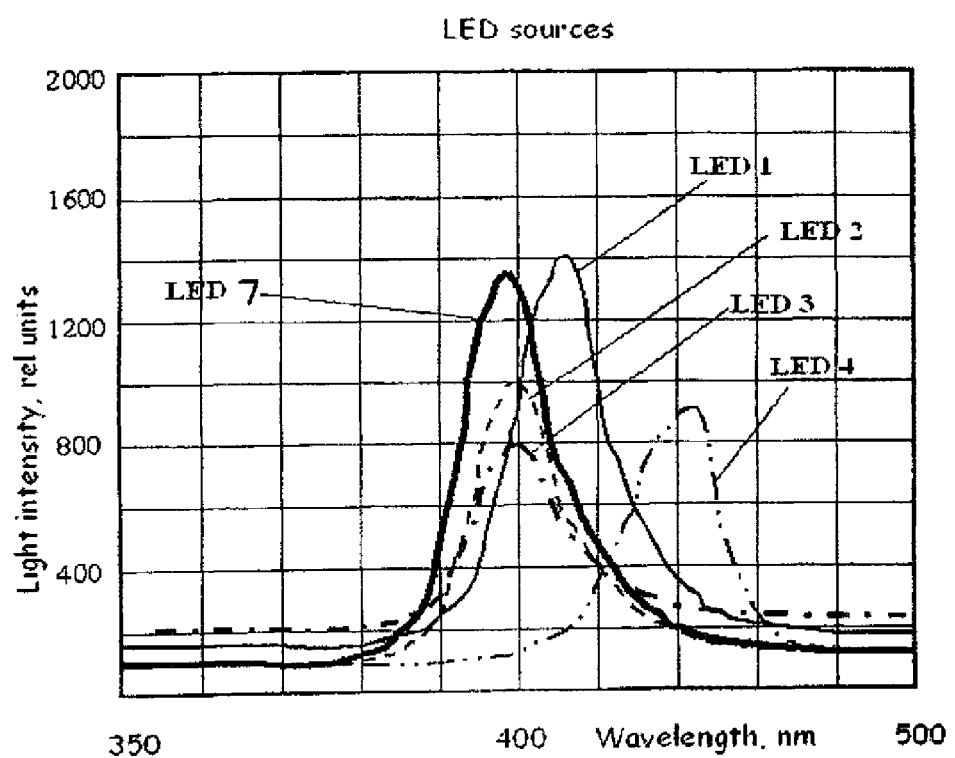
FIG. 11 is a graph of absorbance spectra of several Light Emitting Diode (LED) sources.

A light emitter 25 is a light source in the optical system. As a light source, the LED-7 element is selected. Its optical performance is presented in FIG. 11. For other chemical cell sensors 23 other emitters can be selected, mainly from the group LED.

Figure 6:
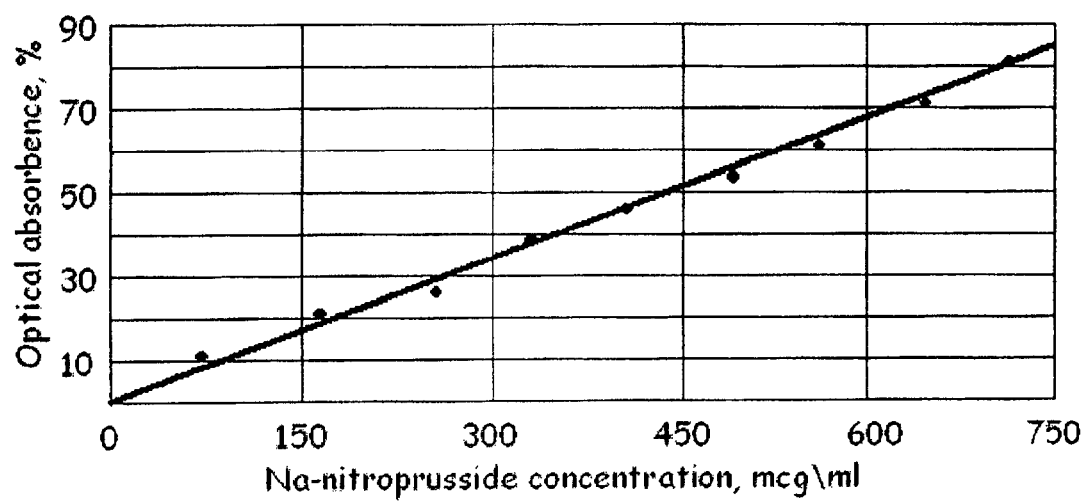
FIG. 6 is a graph of percent optical absorbance vs. Na-nitroprusside concentration in mcg/ml.
Figure 7:
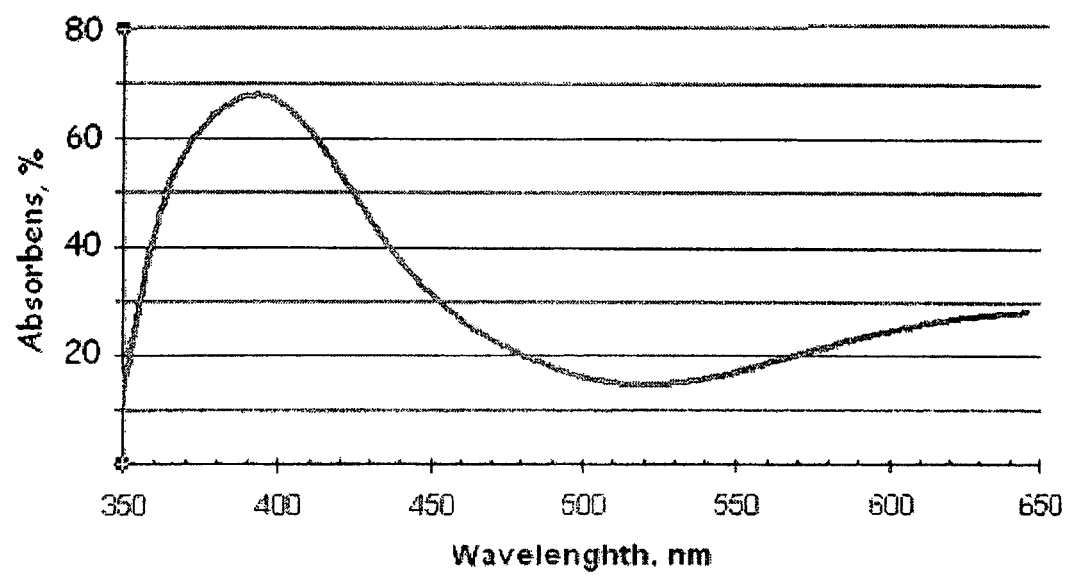
FIG. 7 is an absorbance spectrum

Before testing begins, a measurement is recorded of the optical absorption of the solution 35 (the first measuring) as a blank. The absorbance spectrum of the chemical cell 23, including sodium nitroprusside and sodium hydroxide in the water-ethanol mixture is presented in FIG. 7:

The spectrum has a maximum absorption at 393 nm. An absolute value of the maximum depends on the concentration of sodium nitroprusside in the solution 35. The dependence of maximum absorption (an optical density) on the concentration of sodium nitroprusside is presented is presented below in FIG. 6.

To determine acetone in the exhaled air the following concentrations of the solution 35 are selected:

| | |
|---|---|
| Sodium-nitroprusside | 450-600 micrograms/ml, |
| Sodium hydroxide | 630-850 micrograms/ml. |

The device 10 is now ready to measure acetone in exhaled air. Dosator 11 is filled with 1 liter of the exhaled air that enters device 10 through inlet 12 and is delivered to dosator 11 through first air tube 26. Dosator 11 is controlled by actuator 21 that controls one or more air regulator valves. Once dosator 11 is filled, actuator 21 restricts additional air from exiting dosator 11. Actuator 21 allows air to exit dosator 11 through second air tube 27 that is directed into chemical cell inlet 28 and ultimately into solution 35 in chemical cell 23 and exits through chemical cell outlet 30 and is released to the atmosphere. Exalted acetone enters into a chemical reaction with the solution 35 and forms a new chemical substance as demonstrated by reaction scheme 1.

Device 10 has operative electronics and microprocessor components such that when dosator 11 is empty, light emitter 25 turns on. The optical absorption of sodium nitroprusside, which remained after the formation of the new chemical substance (the second measuring) is measured and recorded.

After reaction with acetone in exhaled air, the absorption peak of sodium nitroprusside is reduced. The optical components of device 10 measure the absorbance of solution 35 after reaction with acetone in exhaled air.

Figure 9:
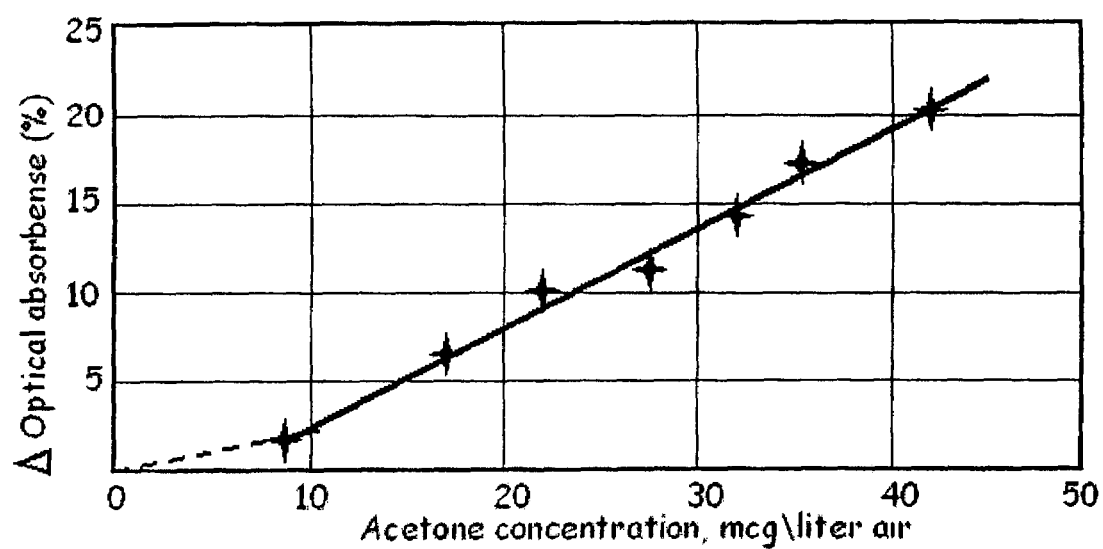
FIG. 9 is a graph correlating the change in optical absorbance vs. acetone concentration in mcg/liter in exhaled air.

The difference between the first measurement i.e. before reaction with acetone in exhaled air, and second measurement i.e. after reaction with exhaled air is processed in a microprocessor 22 that has computer readable information for corresponding the concentration of acetone in the exhaled air based on the change in absorbance of solution 35. Laboratory results are presented in FIG. 9.

The present device, system, and method correlate the concentration of the exalted acetone proportional to the concentration of glucose in the blood.

Experimental Corrolation

Measurement of the exalted acetone (two voluntaries) showed the presence of acetone in amounts of 27 and 42 mg/l. For determination of glucose, the published data on the correlation between the content of exalted acetone and the content of glucose in the blood are used.

Figure 8:
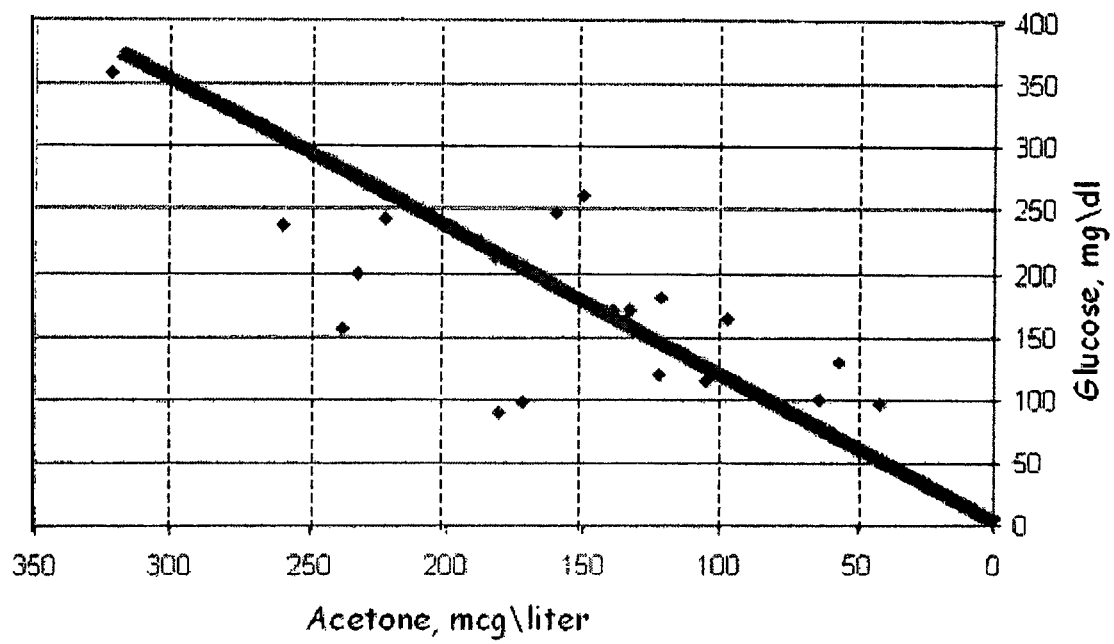
FIG. 8 is a scatterplot with linear representation of best fit line correlating blood glucose concentration with acetone concentration in exhaled air.

FIGS. 8 and 10 present data on the correlation. In accordance with these data the content of glucose in the blood of patients is found equal to 70 and 105 mg/dl. Measurement of glucose with a standard device has confirmed the reliability of the results. A comparison was made with a standard device Accu-Check Go® (Roche Diagnostics, Indianapolis, Ind.). The difference between the device of the invention and the Accu Check® was 19% for one patient and 4% for the second patient.

The analytical result is achieved by the registration of molecular spectrum, followed by intensification of an electrical signal.

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

We claim:

1. A device for measuring the concentration of acetone in exhaled air in order to determine the content of glucose in the blood, comprising:
   (a) an inlet configured for receiving expirated air;
   (b) a dosator configured for receiving air from said inlet;
   (c) an actuator configured for receiving air from said dosator with substantially the same volume for one or more measurements, said actuator interrupts air from said inlet when said dosator reaches a specified volume;
   (d) a chemical cell containing a solution and comprising a hollow truncated cone that is vertically orientated;
   (e) a light emitter constructed and arranged for emitting light of a frequency enabled to pass through said solution;
   (f) an optical sensor; and
   (g) a microprocessor;
   wherein said microprocessor produces an output correlating measurements of said optical sensor with blood glucose concentration.

2. The device of claim 1 wherein said actuator is coupled to a valve.

3. The device of claim 1, wherein said solution of said chemical cell selectively reacts with acetone from expired air.

4. The device of claim 1 wherein said solution contains a solute selected from the group consisting of Sodium Iodate, Sodium Nitroprusside, Metadiamine, Phenyl-hydrazone, Furfural, o-Nitrobenzaldehyde, and combinations thereof.

5. The device of claim 1 further comprising an output of a numerical value, wherein said numerical value is produced by said microprocessor and correlates the difference in optical absorbance of an unreacted solution with a solution reacted with acetone from exhaled air to produce an output congruous with blood glucose concentration.

6. The device of claim 5, wherein said output is displayed on a screen, transmitted wirelessly to a receiving device, or combinations thereof.

7. A method for determining acetone concentration in exhaled air and correlating said acetone concentration with blood glucose levels, said method comprising:
(a) providing a device according to claim 1;
(b) initiating a blank reading spectral of said chemical sensor solution;
(c) instruction a user to inhale and hold their breath for about 3-5 seconds;
(d) having said user exhale into an inlet of said device;
(e) taking a spectral reading of said chemical cell solution after reaction with acetone in expired air;
said device measures the change in absorbance from said blank reading with said spectral reading after reaction of said chemical cell solution with acetone from expired air and said device produced an output whereby said difference in absorbance is correlated with blood glucose concentration of said user.

* * * * *